United States Patent [19]

Johnson et al.

[11] Patent Number: 5,464,739
[45] Date of Patent: Nov. 7, 1995

[54] COMPOSITION METHOD FOR DETERMINING THE PRESENCE OF LEUKOCYTE CELLS, ESTERASE OR PROTEASE IN A TEST SAMPLE

[75] Inventors: Gary M. Johnson, Elkhart; Robert J. Schaeper, South Bend, both of Ind.

[73] Assignee: Bayer Corporation, Elkhart, Ind.

[21] Appl. No.: 293,723

[22] Filed: Aug. 22, 1994

[51] Int. Cl.$^6$ ............... C12Q 1/00; C12Q 1/44; C07C 59/08
[52] U.S. Cl. ............... 435/4; 435/19; 435/805; 436/903; 560/1; 562/589
[58] Field of Search ............... 435/4, 19, 23, 435/805; 436/63, 903; 560/1; 562/589

[56] References Cited

U.S. PATENT DOCUMENTS

| | | | |
|---|---|---|---|
| 4,064,236 | 12/1977 | Dorn | 424/177 |
| 4,299,917 | 11/1981 | Berger | 435/19 |
| 4,421,761 | 12/1983 | Nagai | 424/275 |
| 4,637,979 | 1/1987 | Skjold | 435/19 |
| 4,657,855 | 4/1987 | Corey | 435/19 |

OTHER PUBLICATIONS

Dorn C., Proteinase Inhibitors: Inhibitors of Elastase J. of Medicinal Chem vol. 20 #11 (1977) pp. 1464–1468.
Moorlag H., Pig Liver Esterase Catalyzed Hydrolyses . . . J Org Chem 55 (1990) 5878–5881.
Moorlag H., PLE Catalyzed Hydrolyses of α. . . Tetrahedron vol. 2 No. 7 pp. 705–720 1991.
Kraicsovits F., Effect of the Alcohol Moiety . . . 11 Int Symp on Chem Sym Papers 1 (1978) pp. 37–40.
Harper J., Active Site Mapping of the Sering Proteases . . . Biochem (1984) 23 2995–3002.
Digenis G., Peptidyl Carbamates Incorporating . . . J Med Chem (1986) 29 1468–1476.
Krantz A., Design & Synthesis of 4H–3,1–Benzoxazin . . . J Med Chem (1990) 33 pp. 464–479.
Ingles D., The Stereospecificity of α–Chymotrypsin Biochem J (1968) 108 pp. 561–569.

Primary Examiner—William H. Beisner
Assistant Examiner—Ralph Gitomer
Attorney, Agent, or Firm—Roger N. Coe

[57] ABSTRACT

A composition and method for determining the presence of leukocyte cells, esterase or protease in a test sample are disclosed. The composition contains a lactate ester having the structure

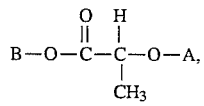

wherein A is an alcohol blocking group, and wherein B-O- is a residue of compound B-OH and provides a detectable response when the lactate ester is hydrolyzed; and a buffer. One class of lactate ester has the structure

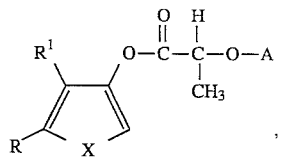

wherein X is O, S or $NR^2$, R is aryl or lower alkyl, $R^1$ is hydrogen or lower alkyl, and $R^2$ is hydrogen, lower alkyl or aryl.

54 Claims, No Drawings

5,464,739

COMPOSITION METHOD FOR DETERMINING THE PRESENCE OF LEUKOCYTE CELLS, ESTERASE OR PROTEASE IN A TEST SAMPLE

FIELD OF THE INVENTION

The present invention relates to a novel composition, test device and method of assaying a test sample for the presence of leukocyte cells, esterase or protease. More particularly, the present invention relates to using a lactate ester, like a hydroxy-protected 5-phenyl-3-hydroxy-pyrrolyl-(L)-lactate ester, as a chromogenic substrate for a serine protease-based enzyme. The lactate esters undergo a detectable or measurable response upon contact with a test sample containing leukocyte cells, esterase, elastase or protease. A composition comprising a lactate ester and a diazonium salt coupling agent provides a more sensitive assay for leukocyte cells, esterase or protease, therefore improving detection of leukocyte cell concentrations. The increased sensitivity demonstrated by a combination of the lactate esters of the present invention and a diazonium salt coupling agent provides an improved method of assaying for leukocyte cells, esterase or protease in a test sample, such as a biological fluid, like urine. The lactate esters are particularly useful in detecting leukocyte cell concentrations in a test sample by a simple dip-and-read method using a dry phase test strip which incorporates a lactate ester of the present invention.

BACKGROUND OF THE INVENTION

The presence of an abnormally high level of leukocyte cells in the urine of an individual is indicative of a pathological condition, such as a kidney or urogenital tract infection. The detection of leukocyte esterase in urine is an indirect test for bacteriuria (i.e., an abnormally high level of bacteria), and therefore infection. Accordingly, an accurate urine leukocyte cell assay, or leukocyte esterase assay, is valuable to a physician in the diagnosis and treatment of kidney and urogenital tract infections.

Traditionally, technicians relied upon visual techniques to count leukocyte cells either in urine sediment or in uncentrifuged urine. The conventional visual technique requires expensive equipment, such as a centrifuge and microscope, in addition to an inordinate amount of technician time. An additional disadvantage of the visual technique is that only intact leukocyte cells can be counted. However, leukocyte cells in the urinary system are subject to extensive cell lysis. For example, in a urine having an abnormally high pH, the half life of a leukocyte cell can be as low as 60 minutes. Since lysed leukocyte cells escape detection in the visual technique, an erroneously low, or a false negative, result for leukocyte cells can result.

A visual examination for leukocyte cells in urine can be performed on uncentrifuged urine or on urine sediment. The latter method requires centrifuging the urine sample, isolating the sediment, then visually inspecting the sediment, wherein the technician counts the number of leukocyte cells appearing in the viewing field. This visual technique is complicated by the presence of other components in the urine sediment, such as epithelial cells and salt particles. The presence of various urine sediment constituents, coupled with other factors, like a nonhomogeneous sample or differing optical powers between microscopes, can lead to substantial assay errors.

Therefore, a quick, easy method of assaying for leukocyte cells, which eliminates the need for time-consuming counting techniques and expensive equipment, and which provides an accurate assay for intact and lysed leukocyte cells, would constitute a significant advance in the art. The present invention provides such an advance. Moreover, because the present invention is based on the enzymatic activity of esterase or protease in leukocyte cells, and not on the ability to visually observe and count intact leukocyte cells, the method is free of the assay inaccuracies described above.

Prior to the present invention, compositions and methods of determining the presence or concentration of leukocyte cells, esterase or protease in a test sample utilized chromogenic esters which produced an alcohol product as a result of hydrolysis by an esterase or protease. The intact chromogenic ester has a color different from the alcohol hydrolysis product. The color change generated by hydrolysis of the chromogenic ester therefore provides a method of detecting the presence or concentration of esterase or protease, which in turn is correlated to the presence or concentration of leukocyte cells. Many of these prior compositions used accelerator compounds and diazonium salt coupling agents in conjunction with the chromogenic ester to improve assay response.

A present day urine assay for leukocyte esterase, and therefore indirectly for leukocyte cells, is a dry phase test strip termed LEUKOSTIX®, available from Miles, Inc., Elkhart, Ind. This test strip detects esterase activity released from granules of leukocyte cells into the urine. The released esterase is termed "human leukocyte elastase" (HLE), and is a serine protease-based enzyme.

In the assay for leukocyte esterase or HLE using a LEUKOSTIX® strip, the enzyme hydrolyzes a—chromogenic ester incorporated into the strip to form a pyrrole compound, which in turn reacts with a diazonium salt to form a highly colored azo dye. The degree and intensity of the color transition is proportional to the amount of leukocyte esterase or HLE in the urine, which in turn, is proportional to the number of leukocyte cells in the urine.

The reaction chemistry of the LEUKOSTIX® test strip is illustrated as follows:

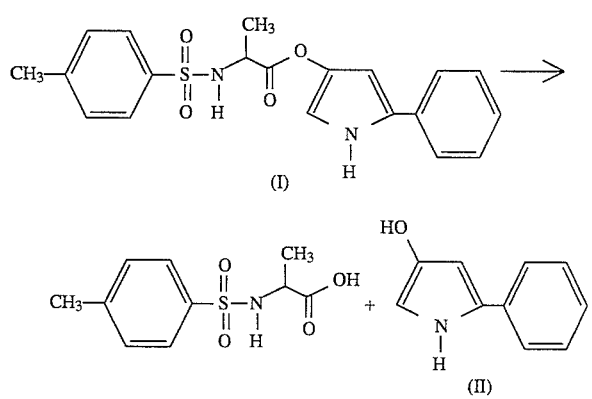

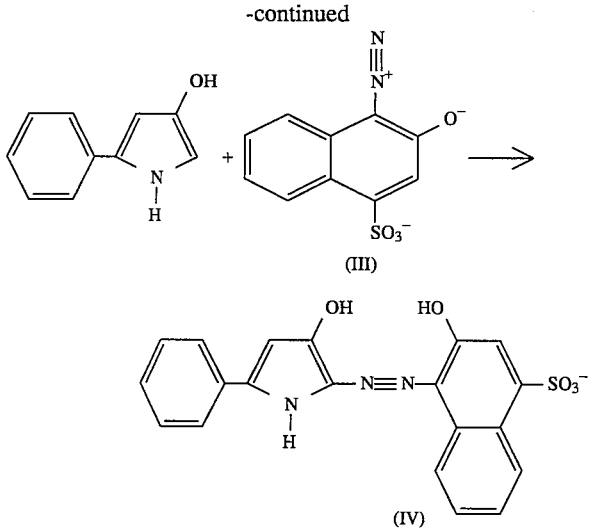

In particular, the LEUKOSTIX® assay for leukocyte esterase is based on the splitting, i.e., hydrolysis, of the 3-hydroxy-5-phenyl-pyrrole-N-tosyl-L-alanine ester (I) by an enzyme or enzymes to form 3-hydroxy-5-phenyl-pyrrole (II). The hydroxy-pyrrole (II) then reacts with a diazonium salt (III) (e.g., 1-diazo-2-naphthol-4-sulfonic acid) to produce azo dye (IV) having a purple color.

The reacted LEUKOSTIX® test strip is matched to a color chart having four color blocks of increasing color intensity from trace to 3+, which in an average urine represents a leukocyte cell concentration of about 10 to greater than 500 cells/µL (microliter), or 30 to greater than 1500 ng/mL (nanograms per milliliter) of HLE. In low specific gravity test samples, even smaller concentrations of HLE can be detected.

The intensity of the color is proportional to the amount of enzyme (e.g., HLE) present in the urine sample and, therefore, is directly related to the number of leukocyte cells in the urine. An assay which generates a color of 1+ or more is a definite indication that a significant number of leukocyte cells are present in the urine sample.

The present day composition and method of assaying for leukocyte cells is disclosed in Corey et al. U.S. Pat. No. 4,657,855 and Skjold et al. U.S. Pat. No. 4,637,979. As disclosed therein and as discussed above, the current LEUKOSTIX® test strips rely upon an amino acid ester, and in particular an alanine ester, to provide a color transition in the assay for leukocyte cells. Other patents related to assaying for an esterase or protease enzyme include Hugl et al. U.S. Pat. Nos. 4,806,423 and 4,814,271.

In contrast to present-day compounds and compositions used to assay for HLE and leukocyte cells, the method and test device of the present invention utilize a lactateester, like a hydroxy-protected 5-phenyl-3-hydroxy-pyrrolyl-L-lactate. The present lactate esters have increased reactivity relative to the corresponding alanine esters, such as the N-tosyl alanine ester having structural formula (I) depicted above. A combination of the present lactate esters and a diazonium salt coupling agent also provide a more sensitive assay for HLE. The lactate esters, like the alanine esters, undergo a detectable or measurable response, like a color transition, upon contact with leukocyte cells, esterase or protease. The response is proportional to the concentration of leukocyte cells, esterase or protease in a test sample.

Other patents and publications disclose the hydrolysis of indoxyl- and thioindoxyl-alanine esters to generate a color transition or other detectable response. These references include GB Patent No. 1,128,371; Janoff et al., *Proc. Soc. Exper. Biol. Med.*, 136, pp. 1045–1049 (1971); Sweetman et al., *Jour. Hist. Soc.*, 22, pp. 327–339; and Berger et al. U.S. Pat. No. 4,278,763.

To date, no known patent or publication discloses the use of a lactate ester as an enzyme substrate in the assay for leukocyte cells, esterase or protease. Dorn et al. U.S. Pat. No. 4,064,236 and Dorn et al., *J. Med. Chem.*, 20, pp. 1464–1468 (1977) disclose inhibitors for pancreatic and granulocyte elastase. Some of the compounds contain a lactate moiety at the non-scissle and scissle points of cleavage. These compounds range from being strong to very weak inhibitors. These compounds do not contain activated leaving groups and are designed primarily as inhibitors to elastase with carbazate esters resembling alanine present at non-hydrolytic sites to increase selectivity for inhibiting elastase. Similarly, Japanese Kokai JP 52/057,121 discloses lactoyl-polypeptide compounds exhibiting potent antipepsin and anticathepsin inhibitory activity, wherein the lactate moiety again is incorporated in an inhibitory capacity. In contrast, the present lactate esters are chromogenic substrates having high esterase (HLE) enzymatic activity, and the ester linkage of the chromogenic lactate ester is the hydrolysis site.

J. Dufer et al., *Ann. Pharm. Fr.*, 31, pp. 441–450 (1973) discloses a 9-methoxyellipticine lactate salt having a decreased esterase activity in lymphocytes, and which was used against acute myeloblastic leukemia. The disclosed lactate salt is used as a solubilizing component for the ellipticine, and has an inhibitory activity for esterase.

H. Moorlag et al., *J. Org. Chem.*, 55, pp. 5878–5881 (1990) and H. Moorlag et al., *Tetrah.; Assym.*, 2, pp. 705–720 (1991) disclose the enzymatic hydrolyses of a variety of α-substituted mandelic esters, α-substituted lactic esters and racemic α-substituted α-hydroxy esters using pig liver esterase to determine enantioselectivity. Pig liver esterase showed no enantioselectivity for the α-substituted lactic esters.

F. Kraicsovits et al., *Symp. Pap. IUPAC Int. Symp. Chem. Nat. Prod.*, 1, pp 37–40 (1978) discloses the effect of structure on the reactivity of substrates in the presence of the serine protease, chymotrypsin, wherein particular non-amino acid substrates contained the lactate moiety. In these examples, the lactate moiety is not at the hydrolysis site, but rather one residue removed from the hydrolysis site.

Publications such as J. W. Harper et al., *Biochem.*, 23, pp. 2995–3002 (1984); G. Digenis et al., *J. Med. Chem.*, 29, pp. 1468–1476 (1986); A. Krantz et al., *J. Med. Chem.*, 33, pp. 464–479 (1990); and D. W. Ingles et al., *Biochem. J.*, 108, pp. 561–569 (1968) disclose that the natural substrate at the HLE cleavage site is an amino acid, such as alanine or valine.

In particular, the D. W. Ingles et al. publication discloses rates of deacylation of acyl-α-chymotrypsins wherein the nitrogen-hydrogen bonding capacity of the acylamino group of the substrate has been eliminated by replacing the nitrogen with an oxygen (i.e., conversion to a lactate). When L-phenyl-alanyl was changed to L-phenyl-lactyl, the substitution resulted in a ten fold decrease in the enzymatic rate. Stereospecificity also decreased by a magnitude of up to 700 in replacing the amino NH moiety with a lactate OR moiety, wherein R is acetate or carboxyphenyl.

Other publications disclosing the hydrolysis of lactates and/or alaninates include:

J. Suh et al., *J. Am. Chem. Soc.*, 107, pp. 4530–4535 (1985);

J. Suh et al., *J. Am. Chem. Soc.*, 98, pp. 1940–1947 (1976);

J. Sub et al., *Biochemical and Biophysical Research Communications*, 64, pp. 863–869 (1975);

L. C. Kuo et al., *J. Mol. Biol.*, 163, pp. 63–105 (1983);

S. J. Hoffman et al., *J. Am. Chem. Soc.*, 105, pp. 6971–6973 (1983);

P. L. Hall et al., *J. Am. Chem. Soc.*, 91, pp. 485–461 (1968); and

M. W. Makinen et al., *Proc. Natl. Acad. Sci. USA*, 73, pp. 3882–3886 (1976).

Therefore, in order to detect the onset and to monitor the progression of a kidney or urogenital tract infection, an accurate and sensitive assay.of urine for leukocyte cells, esterase or protease is needed for both laboratory and home use. The assay should permit the detection and measurement of the leukocyte cells, esterase or protease in the test sample such that a correct diagnosis can be made and correct medical treatment implemented, monitored and maintained. In addition, it would be advantageous if the assay method utilizes a dry phase test strip in a dip-and-read format for the easy and economical determination of leukocyte cells or HLE in urine.

Present day test strips for leukocyte cells need improvement in the areas of sensitivity and speed of assay. Therefore, it would be a significant advance in the art of diagnostic assays if test strips for leukocyte cells were more sensitive to low concentrations of leukocyte cells and provided assay results in about 60 seconds. It was towards achieving these improvements that investigations resulting in the composition, device and method of the present invention were directed.

The method of the present invention provides a fast, accurate and trustworthy assay for leukocyte cells, esterase or protease by utilizing a test strip having a test pad comprising a suitable carrier matrix incorporating a reagent composition of the present invention. The reagent composition comprises a lactate ester, and in particular, a hydroxy-protected 5-phenyl-3-hydroxy-pyrrolyl-L-lactate. The composition further comprises a buffer, and optionally can include an accelerator compound and/or a diazonium salt coupling agent. The reagent composition is sensitive to trace concentrations of leukocyte cells, esterase or protease. The present reagent composition enhances the sensitivity of the assay for leukocyte cells, esterase or protease, thereby providing a more accurate and trustworthy assay.

No known method of assaying urine or other test samples for leukocyte cells, esterase or protease used a reagent composition comprising a lactate ester of the present invention.

SUMMARY OF THE INVENTION

In brief, the present invention is directed to a new and improved composition, test device and method of determining the presence or concentration of a predetermined component in a test sample. The device includes a test pad comprising a carrier matrix. The carrier matrix incorporates a reagent composition capable of interacting with a predetermined test sample component to produce a detectable response. For home use, the reagent composition produces a visually detectable response. For laboratory use, the reagent composition produces a response that is detectable visually or instrumentally. The carrier matrix of the test pad comprises a bibulous material, such as filter paper; a nonbibulous material, such as a strip, layer or membrane of a polymerized material; or a combination thereof. A reagent composition is homogeneously incorporated into the carrier matrix, and the carrier matrix holds the reagent composition homogeneously throughout the carrier matrix while maintaining carrier matrix penetrability by the predetermined component of the test sample.

More particularly, the present invention is directed to a method of assaying urine for leukocyte cells, esterase or protease by utilizing a new and improved reagent composition. The reagent composition comprises: (a) a lactate ester capable of generating a detectable response upon interaction with leukocyte esterase; and (b) a buffer.

The term "detectable response" as used herein means a change in, or an occurrence of, a parameter in a test device. The detectable response is capable of being perceived, either visually or instrumentally. The magnitude of the detectable response is proportional to the presence and concentration of a specific analyte in an aqueous test sample. Exemplary, but nonlimiting, detectable responses include a change in, or an occurrence of, color, fluorescence, reflectance, pH, chemilumnimescence, spectrophotometry or colorimetry.

In a preferred embodiment, the reagent composition comprises: (a) a lactate ester having the structural formula (V)

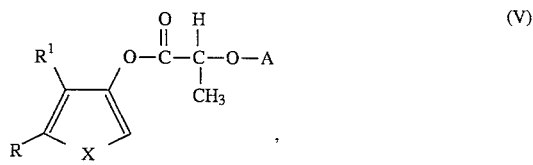

wherein A is an alcohol blocking group; X is O, S, or $NR^2$; R is aryl or lower alkyl; $R^1$ is hydrogen or lower alkyl; and $R^2$ is hydrogen, lower alkyl or aryl; and (b) a buffer.

With respect to stereochemistry, the lactate ester can be in the L-form, the D-form, or a racemic mixture of the D and L-forms. The L-form is preferred. The composition optionally can include an accelerator compound, such as an alcohol having three to about 15 carbon atoms, and/or a diazonium salt coupling agent.

The method comprises contacting a test sample with the reagent composition, or a test device incorporating the reagent composition, then observing and measuring a detectable response, such as a color transition, for the presence or concentration of leukocyte cells, esterase or protease.

In accordance with an important feature of the present invention, a more accurate and reliable assay for leukocyte cells, esterase or protease in a test sample is achieved because the reagent composition exhibits an improved sensitivity to the analytes of interest in comparison to present-day compositions used to assay for leukocyte cells, esterase or protease. Therefore, by utilizing the reagent composition of the present invention, which comprises a lactate ester and, optionally, a diazonium salt coupling agent, the assay for leukocyte cells, esterase or protease, at trace through high concentrations, is more accurate.

Therefore, one aspect of the present invention is to provide a simple, accurate and reproducible method of assaying urine or other liquid test samples for leukocyte cells, esterase or protease.

Another aspect of the present invention is to provide a method of assaying urine for leukocyte cells, esterase or protease by utilizing a reagent composition that provides increased sensitivity and accuracy in the assay for HLE.

Another aspect of the present invention is to provide a new and improved test device for interaction with HLE in a test sample to produce a visible change in the test device, such as a change in color, which is indicative of the concentration of HLE in the test sample.

Yet another aspect of the present invention is to provide a sensitive method of detecting and assaying urine for HLE in a concentration range of about 5 to about 500 ng/mL, and correlating the assay to the concentration of leukocyte cells (i.e., about 2 to about 175 cells/μL) in the urine.

DETAILED DESCRIPTION OF THE PREFERRED EMBODIMENTS

In accordance with the method of the present invention, the assay of urine for leukocyte cells, esterase, protease or HLE is accomplished by utilizing a reagent composition comprising a lactate ester, a buffer, and optionally, an accelerator compound and/or a diazonium salt coupling agent. By employing a reagent composition of the present invention, the lactate ester, such as the lactate ester of structural formula (V), is hydrolyzed by the leukocyte esterase (HLE) to provide, for example, the hydroxy-pyrrole compound of structural formula (II), which in turn can interact with an optional diazonium salt to form an azo dye. The lactate esters of the present invention are readily hydrolyzed by HLE to generate a measurable color transition or other detectable response within about 60 to about 120 seconds.

The reagent composition of the present invention, which is capable of detecting HLE and therefore is capable of detecting leukocyte cells, comprises a lactate ester having the general structural formula (VI)

$$B-O-\overset{O}{\underset{}{\overset{\|}{C}}}-\overset{H}{\underset{CH_3}{\overset{|}{C}}}-O-A, \qquad (VI)$$

wherein A is an alcohol blocking group and B is a moiety capable of providing a detectable response, preferably a chromogenic response, when the lactate ester of structural formula (VI) is hydrolyzed to generate the compound B-OH. The lactate ester can be the D-form, the L-form or a racemic mixture of the D and L-forms. The L-form is preferred.

The moiety B-O- of the compound of structural formula (VI) is defined as the residue of a compound B-OH. The moiety B-O- therefore can be the residue of a substituted or unsubstituted pyrrole, thiophene or furan, for example. Other exemplary compounds having a residue B-O- include, but are not limited to, an azoresorcinol ester, a phenoxy ester (with an oxidative coupler), a leukoindophenol ester, an azo dye ester, 5-(4-hydroxy-3,5-dimethoxyphenylmethylene)-2-thioxothiazoline-3-acetic acid, a 2-substituted-6-hydroxy-benzothiazole derivative disclosed in WO 90/00618 and EP 399 490 (both incorporated herein by reference) having the structure

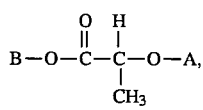

wherein:

a) at least one of the carbons of positions 4, 5, 6 or 7 is linked to a chemical moiety containing an anion group which is attached to the benzene ring; and;

b) the carbon at position 2 is linked to a chemical moiety comprised of at least two atoms which extend resonance of the benzothiazole ring system; and, c) a nitrogen atom is located at position 3; and d) a sulfur atom is located at position 1. A ω-nitrostyryl ester, a resorufin ester, an acridinone, a merocyanine, an 8-hydroxy-2H-dibenz-(b,f)azepin-2-one, a dibenzo azepinone, a dibenzothiazepinone, a coumarin ester, or a chemiluminescent compound disclosed in Schaap U.S. Pat. Nos. 4,857,652 and 4,962,192, incorporated herein by reference.

A preferred lactate ester has the general structural formula (V)

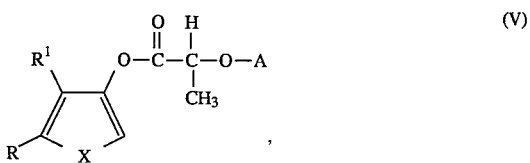

wherein A is an alcohol blocking group, X is O, S or $NR^2$, R is aryl or lower alkyl, $R^1$ is hydrogen or lower alkyl, and $R^2$ is hydrogen, lower alkyl or aryl. The lactate ester of general structural formula (V) is hydrolyzed by the enzyme leukocyte esterase or HLE to generate a hydroxy-compound, such as the hydroxypyrrole (II).

The lactate ester (V) is present in a reagent composition in a concentration of about 0.5 to about 2 mM (millimolar), and preferably about 0.8 to about 1.5 mM. Within this concentration range, a sufficient amount of lactate ester is present in the reagent composition to provide a sufficient color transition or other detectable response to detect trace amounts of leukocyte cells.

The term "lower alkyl", as used herein, is an alkyl moiety containing one to about six carbon atoms. Exemplary, but nonlimiting, lower alkyl groups include methyl, ethyl, n-propyl, isopropyl, n-butyl, sec-butyl, tert-butyl and all isomers of pentyl and hexyl. The lower alkyl group can be unsubstituted, or the lower alkyl group can be substituted, provided the substituent does not interfere with the ability of the composition or test device to detect leukocyte cells, esterase or protease. Exemplary, but nonlimiting, substituents on the alkyl group are alkoxy having one to six carbon atoms, halo, nitro, aryl, and amino.

The identity of the alcohol blocking group, i.e., A, of the lactate ester of general structural formula (VI) is not particularly limited, and can be selected from essentially any blocking group typically used to protect an alcohol moiety.

The alcohol blocking group A typically is the residue of a sulfonyl chloride or a carboxylic acid chloride (i.e., an acyl chloride) and has the structural formula (VII) or (VIII)

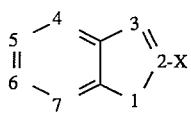

or

wherein $R^3$ is an alkyl group having three to about 22 carbon atoms, and preferably 3 to about 6 carbon atoms, or $R^3$ is an aryl group. When $R^3$ is an alkyl group, the alkyl group can be functionalized, e.g., methoxysuccinyl.

As used herein, the term "aryl" with respect to R, $R^2$ and $R^3$ means any aromatic ring system. Nonlimiting examples of the term "aryl" include 5- and 6-membered aromatic ring systems like pyrrolyl, phenyl and pyridyl, as well as fused aromatic ring systems, like naphthyl. The aromatic ring system can be heterocyclic or carbocylic, and can be substituted or unsubstituted, provided that the substituent groups do not interfere with ability of the chromogenic lactate ester to hydrolyze in the presence of leukocyte cells, esterase or protease. Exemplary, but nonlimiting, substituent groups are alkyl, halo, acyl, aryl, hydroxy, alkoxy, sulfuryl and amino. The aryl group preferably is a phenyl group, either unsubstituted or substituted with a relatively nonreactive group, such as a halo group or an alkyl or alkoxy group having one to about 10 carbon atoms.

Exemplary, but nonlimiting, alcohol blocking groups are residues of p-toluenesulfonyl chloride (tosyl chloride or TsCl), n-propylsulfonyl chloride (n-PrSO$_2$Cl), benzoyl chloride (PhCOCl), carbomethoxyethane sulfonyl chloride and thiophene sulfonyl chloride. Numerous other specific alcohol blocking groups are known to those skilled in the art and can be used as the A component of the present lactate esters. For example, numerous alcohol blocking groups are disclosed in T. W. Greene et al., *Protecting Groups in Organic Chemistry*, 2Ed., (1991), incorporated herein by reference.

A preferred alcohol blocking group A has the structural formula (VII) and includes the sulfonyl moiety. To achieve the full advantage of the present invention, the alcohol blocking group of structural formula (VII) has a phenyl group as $R^3$, wherein the phenyl group is substituted with a methyl or a methoxy moiety.

A preferred lactate ester of the present invention is a chromogenic compound having the structural formula (IX):

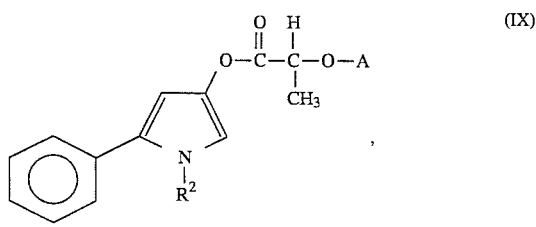

which is the L-form of a lactate ester of general structural formula (V), wherein X is $NR^2$, R is phenyl and $R^1$ is hydrogen. In a more preferred embodiments, the chromogenic lactate ester has structural formula (X):

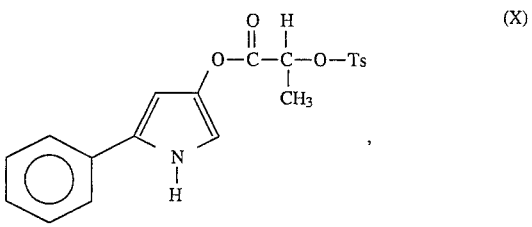

wherein $R^2$ is hydrogen and A is p-toluenesulfonyl (i.e., Ts), i.e., the L-form of the lactate ester of structural formula (V), wherein X is NH, A is Ts, R is phenyl and $R^1$ is H.

Various lactate esters of structural formula (IX), wherein $R^2$ is hydrogen, have been prepared. These chromogenic lactate esters are listed below in Table 1 as the 5-phenyl-3-hydroxy-pyrrole-(L)-lactate esters. The chromogenic lactate esters listed in Table 1 were prepared from the ethyl ester of lactic acid, wherein the hydroxy (i.e., alcohol group) of lactic acid has been blocked. The alcohol-blocked lactic acid ethyl ester starting materials also are listed in Table 1. Each lactate ester is in the L-form.

TABLE 1

| Lactic Acid Ethyl Ester Analogs | 5-Phenyl-3-hydroxy-pyrrole Lactate Esters |
| --- | --- |
| (L)-Ts—OCH(CH$_3$)CO$_2$Et | Ts-(L)-Lac—OPP (X) |
| (L)-nPr—SO$_2$—OCH(CH$_3$)CO$_2$Et | nPr—SO$_2$-(L)-Lac—OPP (XI) |
| (L)-PhCO—OCH(CH$_3$)CO$_2$Et | PhCO-(L)-Lac—OPP (XII) |
| (L)-MeOSucc—SO$_2$—OCH(CH$_3$)CO$_2$Et | MeOSucc—SO$_2$-(L)-Lac—OPP (XIII) |
| (L)-2-Thiophene-SO$_2$—OCH(CH$_3$)CO$_2$Et | Thiophene-SO$_2$-(L)-Lac—OPP(MV) |

PPO = 5-phenyl-3-hydroxy-pyrrole, Lac = lactate (—OCH(CH$_3$)CO—), Ts = tosyl, PhCO = benzoyl, nPr = n-propyl, MeOSucc = methoxysuccinyl (CH$_3$O(CO)CH$_2$CH$_2$), and SO$_2$ = sulfonyl The synthesis of 3-(O-tosyl-(L)-lactoyl)-5-phenylpyrrole (IX) is typical of the synthetic route used to prepare each lactate ester (X) through (XIV) listed in Table 1, or to prepare other lactate esters having the general structural formula (V) or (VI).

The following examples are provided to demonstrate how to make and use the lactate esters, compositions and test devices of the present invention. Various preferred embodiments are described in experimental detail hereafter. However, the following examples are illustrative only, and are not intended as limiting the scope of the invention disclosed and claimed herein.

In the examples and throughout the specification, the following abbreviations have been used:

| | |
| --- | --- |
| mg = | milligram |
| g = | gram |
| kg = | kilogram |
| cm = | centimeter |
| L = | liter |
| mL = | milliliter |
| M = | molar |
| mM = | millimolar |
| mol = | gram molecular formula (moles) |
| mmol = | gram molecular formula × 10$^{-3}$ (millimoles) |
| aq = | aqueous |
| hr = | hour |

Infrared (IR) spectra were obtained with a Perkin-Elmer Model 710B or 237 infrared spectrophotometer as solutions in CDCl$_3$ unless otherwise noted; the 1602 cm$^{-1}$ band of polystyrene film was used as an external calibration standard. Signals are reported as cm$^{-1}$.

Proton magnetic resonance ($^1$H NMR) spectra were obtained at 300 MHz using a GE GN300NB spectrometer or at 60 MHz using a Varian T-60 spectrometer; spectra were obtained in CDCl$_3$ solution unless otherwise noted. Chemical shifts are reported in parts per million (ppm) downfield from an internal standard (i.e., tetramethylsilane).

Carbon-13 magnetic resonance ($^{13}$C NMR) spectra and DEPT magnetic resonance spectra also were obtained using the GE GN300NB spectrometer with Fourier transform and with full proton broad-band noise decoupling; spectra were obtained in acetone-d$_6$, CD$_3$OD, DMSO-d$_6$ or CDCl$_3$ solution unless otherwise noted. Carbon shifts are reported in parts per million downfield from tetramethylsilane.

Mass spectra (MS) were obtained on a Hewlett-Packard 5985A spectrometer operating in either chemical ionization (CI), electron impact (EI) or fast atom bombardment (FAB) mode. High-resolution mass spectra were obtained on an AEI MS-902 spectrometer. Additional spectra were obtained from the Michigan State University Mass Spectroscopy Facility, East Lansing, Mich. 48824.

Optical rotations were obtained on a Model 141 Polarimeter, available from Perkin-Elmer Corporation.

The chromogenic lactate esters (X)–(XIV) were prepared to illustrate synthesis of the lactate esters of the present invention. While these examples disclose specific starting materials and lactate esters, it is envisioned that the synthetic procedures are applicable to a broad range of species included within the generic class of lactate esters of structural formula (VI).

EXAMPLE 1

Synthesis of the Lactate Ester of Structural Formula X

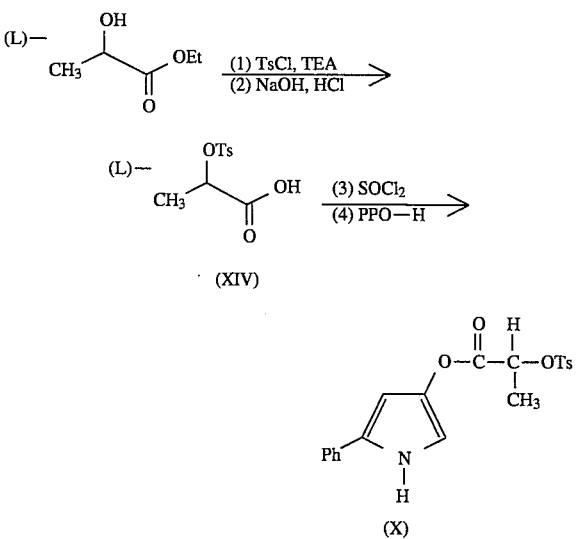

Tosyl chloride (TsCl) (8.1 g, 42.3 mmol) was added with stirring to a solution of the ethyl ester of (L)-lactic acid (5.0 g, 4.81 mL, 42.3 mmol) in methylene chloride (CH$_2$Cl$_2$) (50 mL), which was chilled to 0° C. (ice-bath) under an argon blanket. Triethylamine (TEA) (5.57 g, 7.67 mL, 55.0 mmol) was then added, dropwise, to the resulting solution. The resulting reaction mixture then was stirred for seven hours at 0° C. The reaction mixture next was poured over a solution of 1M aqueous hydrochloric acid (aq HCl) (75 mL) and ice (75 g). The CH$_2$Cl$_2$ organic layer was separated from the HCl layer, then the organic layer was dried over magnesium sulfate (MgSO$_4$). After filtering, the organic layer was concentrated in vacuo to yield 10.5 g (91%) of crude (L)-tosyl lactate ethyl ester.

The crude (L)-tosyl lactate ethyl ester (10.5 g, 38.6 mmol) was dissolved in absolute ethanol (12 mL), and the resulting solution was added dropwise via an addition funnel to a chilled (0° C. ice bath) solution of sodium hydroxide (NaOH) (1.8 g, 46 mmol) in distilled water (20 mL) over a fifteen minute time period. After stirring the resulting reaction mixture for five hours under an argon blanket at 0° C., the reaction was carefully quenched by the dropwise addition of concentrated HCl to lower the pH of the reaction mixture to pH 2. Solid sodium chloride (NaCl) then was added to saturate the reaction mixture, and the aqueous layer was extracted four times with 50 mL portions of CH$_2$Cl$_2$. The combined portions of CH$_2$Cl$_2$ were dried over MgSO$_4$, filtered, and concentrated in vacuo to provide 7.17 g (76%) of crude (L)-O-tosyl-lactic acid (XIV).

Under an argon blanket, the crude (L)-O-tosyl-lactic acid (XIV) (1.5 g, 6.15 mmol) was placed in a 25 mL round-.bottomed flask equipped with a reflux condenser. Thionyl chloride (SOCl$_2$) (10.12 g, 6.2 mL, 85 mmol) was added to the flask, then the flask was placed into a preheated (50° C.) oil bath. The contents of the flask were stirred for two hours at 50° C. The flask then was cooled to room temperature, and finally placed in an ice bath. Next, ice cold hexane (25 mL) was added to the flask. No solid product was observed, therefore the solution in the flask was concentrated in vacuo to yield 1.6 g (quant.) of a crude yellow oil, i.e., (L)-O-tosyl-lactic acid chloride.

In a separate flask, pyridine (1.5 mL, 18.6 mmol) was added to a chilled solution (0° C. ice bath) of 5-phenyl-3-hydroxy pyrrole (PPO-H) (986 mg, 6.2 mmol) in CH$_2$Cl$_2$ (30 mL) under an argon blanket, rapidly and dropwise, followed immediately by a rapid dropwise addition of a solution of (L)-O-tosyl-lactic acid chloride (1.6 g, 6.11 mmol) in CH$_2$Cl$_2$ (5 ml). The residual contents then were added dropwise with an additional 5 ml of CH$_2$Cl$_2$. The resulting reaction mixture was stirred for one hour at 0° C., then allowed to warm to room temperature over an approximately one hour time period. The reaction mixture then was stirred overnight at room temperature (16 hr).

Next, the reaction mixture was extracted two times with 25 mL portions of aq. 1M HCl. The combined portions of HCl then were back-extracted with CH$_2$Cl$_2$ (25 ml). The CH$_2$Cl$_2$ extractant finally was extracted two times with 25 mL portions of saturated aqueous sodium bicarbonate. After again back-extracting the aqueous phase with CH$_2$Cl$_2$, the combined portions of CH$_2$Cl$_2$ were treated with norite carbon and MgSO$_4$, then filtered, and finally concentrated in vacuo.

The resulting oil was dissolved in hexane/ethyl acetate (1:1, 25 mL). The resulting solution was treated with norite carbon, then filtered, and finally concentrated in vacuo to yield 1.7 g of solid crude lactate ester (X). The crude lactate ester (X) was triturated with warm hexane (10 mL), then was triturated two times with 8 mL portions of hexane/ethyl acetate (4:1, 2×8 mL). After the organic solvents were decanted, the solid product was dried under vacuum to provide 1.04 g of a pink solid. The pink solid was dissolved in hexane/ethyl acetate (1:1), treated with norite carbon, filtered, and concentrated in vacuo at room temperature to yield 932 mg of lactate ester (X) as a creme colored solid.

The lactate ester of structural formula (X) was analyzed by proton ($^1$H) and carbon-13 ($^{13}$C) nuclear magnetic resonance, elemental analysis (C/H/N), mass spectroscopy (MS), infrared spectroscopy (IR) and optical rotation. The analytical data is summarized below and confirms the structure of lactate ester (X).

$^1$H NMR (CDCl$_3$, ppm): 1.65 (d, 3H), 2.42 (s, 3H), 5.12 (qu., 1H), 6.26 (dd, 1H), 6.84 (dd, 1H), 7.18–7.5 (m, 7H), 7.84 (d, 2H), 8.15 (brs, 1H).

$^{13}$C NMR (CDCl$_3$, ppm): 18.51 (methyl), 21.66 (methyl), 73.96 (CH, lactate), 93.39 (CH, pyrrole), 107.89 (CH, pyrrole), 123.84 (CH, arom.), 126.85 (CH, arom.), 128.12 (CH, arom.), 128.97 (CH, arom.), 129.87 (CH, arom.), 166.68 (C=O).

C/H/N: calc.: C: 62.39, H: 4.97, N: 3.63, S: 8.33; found: C: 62.44, H: 5.03, N: 3.57, S: 8.65.

EI/MS (18 EV, DIP): 385 (M+, 21.8), 227 (2.3), 199 (22.4), 158 (67.5), 155 (BASE), 91 (41.7).

IR: (CDCl$_3$, cm$^{-1}$): 3450, 3022, 1770, 1600, 1570, 1550, 1514, 1450, 1370, 1260, 1240, 1180, 1080, 1020, 980.

Optical rotation ($\lambda$=578) on a 10 mg sample in 1 mL methanol (MeOH) at room temperature in a 1 cm cell: (−64.8°).

EXAMPLES 2–5

Synthesis of the Lactate Esters of Structural Formulae (XI)–(XIV)

The 5-phenyl-3-hydroxy-pyrrole lactate esters of structural formulae (XI)–(XIV) listed in Table 1 were prepared in an essentially identical manner as the chromogenic lactate ester (X) of Example 1. However, different alcohol blocking groups were used, i.e., n-propylsulfonyl, benzoyl, methoxysuccinyl sulfonyl and thiophene sulfonyl, in the synthesis chromogenic of lactate esters (XI)–(XIV), respectively.

The preparation of the lactate esters of structural formulae (XI)–(XIV) was confirmed by the analytical data summarized below.

nPr-SO$_2$-(L)-Lac-OPP (XI)

$^1$H NMR (CDCl$_3$, ppm): 1.10 (t, 3H), 1.75 (d, 3H), 2.20 (m, 2H), 3.30 (m, 2H), 5.35 (qu., 1H), 6.41 (dd, 1H), 6.95 (dd, 1H), 7.20–7.60 (m, 5H), 8.30 (brs, 1H).

$^{13}$C NMR (CDCl$_3$, ppm): 12.87 (methyl), 17.23 (methylene), 18.59 (methyl), 53.64 (methylene), 73.49 (CH, lactate), 98.32 (CH, pyrrole), 107.94 (CH, pyrrole), 123.86 (CH, arom.), 126.90 (CH, arom.), 128.96 (CH, arom.), 166.5 (C=O).

C/H/N: calc.: C: 56.97, H: 5.64, N: 4.15, S: 9.49; found: C: 57.06, H: 5.75, N: 3.87, S: 9.91.

FAB/MS: 337.2 (M+, 55), 159 (BASE).

IR: (CDCl$_3$, cm$^{-1}$): 3400, 3010, 2980, 1768, 1573, 1512, 1454, 1400, 1360, 1254, 1169, 1116, 1084, 984.

Optical rotation ($\lambda$=578) on a 13 mg sample in 1 mL MeOH at room temperature in a 1 cm cell: (−48.5°).

PhCO-(L)-Lac-OPP (XII)

$^1$H NMR (CDCl$_3$, ppm): 1.75 (d, 3H), 5.55 (qu., 1H), 6.40 (dd, 1H), 6.95 (dd, 1H), 7.15–7.7 (m, 8H), 8.1 (d, 2H), 8.2 (brs, 1H).

$^{13}$C NMR (CDCl$_3$, ppm): 17.13 (methyl), 69.08 (CH, lactate), 98.57 (CH, pyrrole), 108.03 (CH, pyrrole), 123.82 (CH, arom.), 126.68 (CH, arom.), 128.41 (CH, arom.), 128.89 (CH, arom.), 129.91 (CH, arom.), 133.33 (CH, arom.), 165.98 (C=O), 166.48 (C=O).

C/H/N: calc.: C: 71.64, H: 5.07, N: 4.18; found: C: 71.92, H: 5.22, N: 4.28.

EI/MS (18 EV, DIP): 333 (M+, 3.1), 177 (42.8), 149 (22.2), 105 (BASE), 77 (0.7).

IR: (CDCl$_3$, cm$^{-1}$): 3400, 3000, 1763, 1723, 1606, 1585, 1573, 1512, 1452, 1318, 1177, 1113.

Optical rotation ($\lambda$=578) on a 12 mg sample in 1 mL MeOH at room temperature in a 1 cm cell: (+13.3°).

MeOSucc-SO$_2$-(L)-Lac-OPP (XIII)

$^1$H NMR (CDCL$_3$, ppm): 1.78 (d, 3H), 1.98 (t, 2H), 825 2.75 (t, 2H), 2.75 (s, 3H), 5.37 (qu., 1H), 6.42 (brs, 1H), 6.98 (brs, 1H), 7.2–7.55 (m, 5H), 8.2 (brs, 1H).

$^{13}$C NMR (CDCl$_3$, ppm): 18.52 (methyl), 28.42 (methylene), 47.29 (methylene), 52.4 (methyl), 74.14 (CH, lactate), 98.37 (CH, pyrrole), 107.93 (CH, pyrrole), 123.89 (CH, arom.), 126.94 (CH, arom.), 128.98 (CH, arom.).

C/H/N: calc.: C: 53.54, H: 4.99, N: 3.67, S: 8.39; found: C: 53.05, H: 5.07, N: 3.41, S: 7.75.

FAB/MS: 381 (M+, 63), 186 (8.5), 159 (BASE), 91 (12), 55 (24.5).

IR: (CDCl$_3$, cm$^{-1}$): 3450, 3000, 1751, 1741, 1572, 1513, 1453, 1439, 1359, 1319, 1255, 1208, 1030, 984.

Optical rotation) ($\lambda$=578) on a 7 mg sample in 1 mL MeOH at room temperature in a 1 cm cell: (−27.1°).

2-Thiophene-SO$_2$-(L)-Lac-OPP (XIV)

$^1$H NMR (CDCl$_3$, ppm): 1.70 (d, 3H), 5.19 (qu., 1H), 6.32 (dd, 1H), 6.85 (dd, 1H), 7.12 (t, 1H), 7.20–7.50 (m, 5H), 7.70 (dd, 1H), 7.79 (dd, 1H), 8.19 (brs, 1H).

$^{13}$C NMR (CDCl$_3$, ppm): 18.44 (methyl), 74.91 (CH, lactate), 98.34 (CH, pyrrole), 107.90 (CH, pyrrole), 123.85 (CH, arom.), 126.85 (CH, arom.), 127.54 (CH, thiophene), 128.95 (CH, arom.), 134.09 (CH, thiophene), 134.71 (CH, thiophene).

C/H/N: calc.: C: 54.1, H: 3.98, N: 3.71, S: 16.98; found: C: 53.4, H: 4.16, N: 3.69, S: 16.81.

EI/MS (18 EV, DIP): 377 (M+, 63.1), 236 (4.4), 191 (13.8), 164 (4.9), 159 (BASE), 147 (66.1), 99 (8.2), 83 (1.1).

IR: (CDCl$_3$, cm$^{-1}$): 3450, 3050, 2940, 1760, 1573, 1509, 1453, 1404, 1378, 1084, 1018.

Optical rotation) ($\lambda$=578) on a 12 mg sample in 1 mL MeOH at room temperature in a 1 cm cell: (−34.3°).

Composition and Test Device

In addition to a lactate ester having a general structural formula (VI), the reagent composition includes a buffer. The buffer is a compound which, when contacted with an aqueous test sample, provides a suitable pH for the reaction. Preferably, the buffer is capable of producing a pH in the range of about 7 to about 10 and, optimally, about 8.5 to about 9.0.

A buffer is included in the reagent composition of the present invention in a concentration of about 200 to about 600 mM, although in particular situations the concentration of the buffer can be above or below this range.

Therefore, a reagent composition of the present invention is buffered to a suitable pH with a buffer such as carbonic acid; BICINE; CHES; borate; phosphate; 2,2-bis(hydroxymethyl)-2,2',2"-nitrilotriethanol; 3,3-dimethylglutaric acid; 3-N-morpholinopropanesulfonic acid (MOPS); 1,3-bis [tris(hydroxymethyl)methylamino]propane (Bis-TRIS); tri (hydroxymethyl)aminomethane (TRIS); tris(hydroxymethyl)aminomethane-maleic acid (TRIS-maleate); tris(hydroxymethyl)aminomethane-malonic acid (TRIS-malonate); 3-N-(trishydroxymethyl)methylamino-2-hydroxypropanesulfonic acid (TAPSO); 2-( [tris(hydroxymethyl)methyl]amino)ethanesulfonic acid (TES); N-2-hydroxyethylpiperazine-N'-2-ethanesulfonic acid (HEPES); and other buffers well known in the art, or combinations thereof. A preferred buffer is boric acid-NaOH.

A composition of the present invention therefore comprises a lactate ester having the structural formula (VI) and a buffer. As previously. discussed, the specific identity of the lactate ester having the structural formula (VI) and of the buffer is not particularly limited. However, preferred lactate esters, like a lactate ester of structural formula (V), and buffers produce optimized assay results, i.e., a detectable and differentiable response in a short time. Assay optimization can be promoted further by including an accelerator compound and/or a diazonium salt coupling agent in the reagent composition.

An "accelerator compound" is any compound that increases the rate of hydrolysis of a lactate ester of structural formula (V) or (VI) by leukocyte cells, esterase or protease. An accelerator compound is selected from such chemically diverse classes of substances as alcohols; and pyridine, imidazole and derivatives thereof. These accelerator compounds are disclosed in Berger et al. U.S. Pat. No. 4,299,917, incorporated herein by reference. Hydrophobic alcohols are especially useful accelerator compounds to increase leukocyte activity. Branched alcohols also have been shown to be useful accelerators of esterase activity. To achieve the full advantage of the present invention, decanol is utilized as the accelerator compound. An accelerator compound is present in the reagent composition in an amount of 0 to about 4% (v/v), and preferably in about 0.1% to about 2% (v/v), of the composition. To achieve the full advantage of the present invention, the accelerator compound is present in an amount of about 1% to about 2% (v/v) of the composition.

The present reagent composition also can include a diazonium salt as a coupling agent. The diazonium salt is present at a concentration of 0 to about 2 mM, and preferably 0.1 to about 1 mM. To achieve the full advantage of the present invention, the diazonium salt coupling agent is present at a concentration of about 0.5 to about 1 mM. The diazonium salt interacts with a hydroxy compound B-OH, such as the hydroxy-pyrrole (II), which is generated by hydrolysis of a lactate ester of structural formula (VI) by leukocyte cells, esterase or protease. The hydroxy compound then interacts with the diazonium salt to yield an azo dye which exhibits a deep, distinctive color, which is indicative of the presence of leukocyte cells, esterase or protease.

Often, the hydroxy compound, such as the hydroxy-pyrrole (II), itself is a distinct ultraviolet (UV) absorbing compound and therefore also can serve as an indicator to detect the presence or concentration of leukocyte cells, esterase or protease in a test sample. The degree and intensity of the color change of the reagent composition increases as the concentration of hydroxy-pyrrole (II) increases. The concentration of hydroxy-pyrrole (II) is directly proportional to the amount of leukocyte cells, esterase or elastase in the test sample. Therefore, the increase in absorbance generated by production of hydroxy-pyrrole (II) in the hydrolysis of chromogenic lactate ester (V) (or by production of the hydroxy compound B-OH in the hydrolysis of chromogenic lactate ester (VI)) can be correlated to the amount of leukocyte cells, esterase or elastase in the test sample. However, a more spectacular blue or red color transition results when a diazonium salt is present to interact with a hydroxy compound B-OH or the hydroxy-pyrrole (II) to form an azo dye. The more spectacular color change provides a more differentiable color change, and accordingly, a more accurate assay.

The diazonium salt coupling agent has a general structural formula

wherein Ar is an aryl group. More particularly, the diazonium salt typically is an aromatic diazonium salt having the general structural formula:

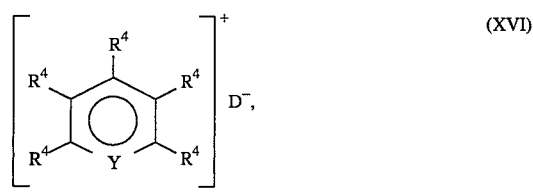

wherein $R^4$, either the same or different, is hydrogen, lower alkyl or aryl, or wherein two adjacent $R^4$ groups together form a fused ring system, with the proviso that one of $R^4$ is $-N^+\equiv N$, i.e., diazonium; Y is N or $CR^5$, wherein $R^5$ is hydrogen or lower alkyl; and $D^-$ is an anion, such as chloride, bromide or other suitable counterion for the diazonium moiety.

The term "fused ring system", as used herein, means two or more aromatic rings that share a pair of carbon atoms. For example, in the diazonium salt having structural formula (XVII),

both G groups together can form a fused ring system, wherein both G groups together constitute $-(CH-)_4$, e.g., the diazonium salt of structural formula (XVIII). The F group is hydrogen, lower alkyl or hydroxy.

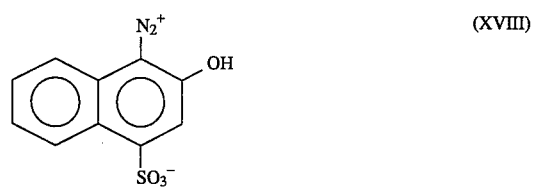

Another example of a fused ring system is the composition of structural formula (XIX),

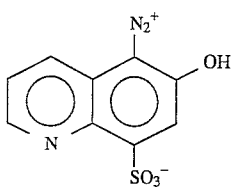
(XIX)

wherein both G groups together constitute -(CH=CH-CH=N)-. Therefore, a fused ring system is polynuclear, aromatic, and heterocyclic or homocyclic.

A diazonium salt which is zwitterionic is a preferred coupling agent. The zwitterionic diazonium compound is a species of diazonium salt wherein the counterion (i.e., the anion) of the diazonium moiety is covalently bound to the ring system. Examples of such anions include, but are not limited to, sulfonate ($SO_3^-$), carbonate ($CO_2^-$) and phosphonate ($PO_3^-$). Zwitterionic diazonium salts have the general structural formula (XVII), illustrated above, wherein F is hydrogen, lower alkyl or hydroxy; D is a covalently bound anion; G, either the same or different, is hydrogen, lower alkyl or aryl, or both G groups together form a fused ring system.

Various diazonium salts are disclosed in Skjold et al. U.S. Pat. No. 4,637,979; Hugl et al. U.S. Pat. No. 4,806,423; and Hugl et al. U.S. Pat. No. 4,814,271, incorporated herein by reference. Specific, nonlimiting examples diazonium salts useful in the composition and method of the present invention are 1-diazo-2-naphthol-4-sulfonate and 1-diazophenyl-3-carbonate. Other nonlimiting examples of diazonium salts are 4-diazo-3-hydroxy-1-naphthylsulfonate (DNSA), 4-diazo-3-hydroxy-7-nitro-1-naphthylsulfonate (NDNSA), 4-diazo-3-hydroxy-1,7-naphthyldisulfonate, 2-methoxy-4-(N-morpholinyl)benzene diazonium chloride, 4-diazo-3-hydroxy-7-bromo-1-naphthylsulfonate, 4-diazo-3-hydroxy-7-cyano-1-naphthylsulfonate, and 4-diazo-3-hydroxy-7-[1-oxopropyl]-1-naphthylsulfonate, illusrated below by structural formulae (XX)–(XXVI), respectively.

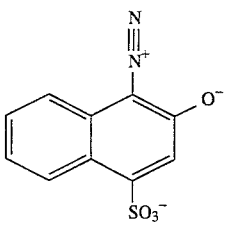
(XX)

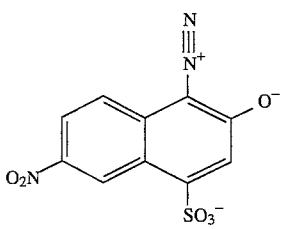
(XXI)

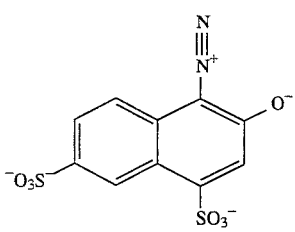
(XXII)

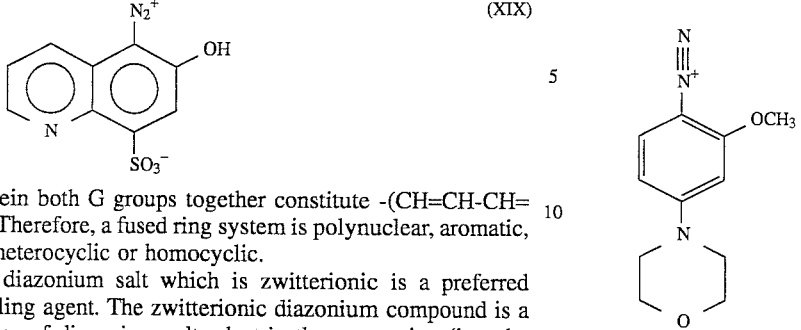
(XXIII)

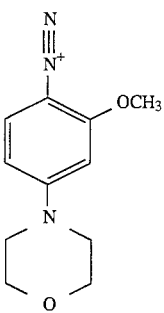
(XXIV)

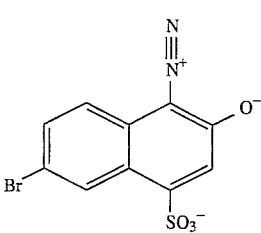
(XXV)

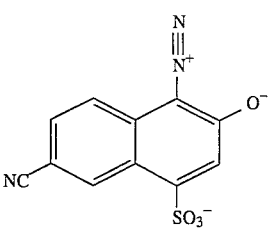
(XXVI)

A preferred diazonium salt is the compound of structural formula (XXI), which enhances the color transition, and accordingly the sensitivity, of the assay for leukocyte cells, esterase or proteaseo Therefore, the reagent composition of the present invention, comprising a lactate ester of structural formula (VI), a buffer, and, optionally, an accelerator compound and/or a diazonium salt coupling agent, is utilized in an improved method to determine the presence or the concentration of leukocyte cells, esterase or protease, or HLE, in liquid test samples. The reagent composition interacts with HLE to hydrolyze the lactate ester of structural formula (VI), which generates a differentiable and measurable response, such as a color transition. The response can be detected visually or by instrument. Furthermore, in addition to the ingredients described above, the reagent composition of the present invention also can include a sufficient amount of various other optional ingredients.

Optional ingredients that do not materially alter the nature or the function of the essential ingredients, and that do not interfere with the assay for leukocyte cells, esterase or protease also can be included in the reagent composition. For example, the reagent composition optionally can include a compound to improve wetting of the test pad of the test device by the liquid sample. This compound typically is an anionic surfactant or a nonionic surfactant. An anionic surfactant, such as long carbon chain sulfates or sulfonates, like pentyl to dodecyl sulfates or sulfonates, dioctyl sodium sulfosuccinate and sodium dodecylbenzene sulphonate, are the preferred surfactants. The surfactant is included in the reagent composition in a concentration of 0% to about 0.4%, and preferably in a concentration of about 0.05% to about 0.2%, by total weight of the reagent composition.

The reagent composition also can include a polymeric material for uniformity of the color transition of the test device. Polymeric materials can include, but are not limited to, polyvinylpyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone of average molecular weight about 10,000 to about 200,000 and available commercially from ISP Corp., New York, N.Y. The polymeric material generally is included in the reagent composition in an amount of 0% to about 4%, and preferably from about 0.5% to about 2%, by total weight of the reagent composition.

The carrier for the ingredients included in the reagent composition comprises water. However, because of the limited water solubility of particular ingredients, organic solvents such as methanol, ethanol, isopropyl alcohol, acetone, dimethylformamide, dimethylsulfoxide, and similar solvents can be included in the carrier. The selection of a suitable organic solvent or solvents, in addition to water, to include in the carrier of the reagent composition is within the capability of those skilled in the art of designing diagnostic assays.

As previously described, the reagent composition undergoes a response, and preferably a color transition, upon contact with a test sample to assay for the presence or concentration of leukocyte cells, esterase or protease. The intensity and degree of the color transition are used to quantitatively determine the concentration of leukocyte cells in the test sample. In accordance with an important feature of the present invention, a reagent composition of the present invention provides a sufficiently resolved and differentiated color transition such that the concentration of leukocyte cells in a test sample can be measured and accurately determined without the use of color-measuring instruments, such as spectrophotometers or colorimeters. However, if desired, such color-measuring instruments can be used to measure the difference in color degree and intensity between the test sample and a solution having a known concentration of leukocyte cells, esterase or protease.

To demonstrate the method of the present invention, a reagent composition comprising a lactate ester of general structural formula (V) and a buffer was used in a dry phase test strip assay for HLE. The reagent composition also can be used in a wet phase assay for HLE. The dry phase or the wet phase assay for HLE can be correlated to the leukocyte cell concentration of the test sample.

A dry phase test strip assay utilizing the present reagent composition is performed in accordance with methods well known in the art. In general, the assay for HLE is performed by contacting the urine or other test sample with an analyte detection device that incorporates the reagent composition. The analyte detection device can be dipped into the test sample, or the test sample can be applied to the analyte detection device dropwise. The resulting change in color of the analyte detection device demonstrates the presence of HLE; and, if so designed, the resulting color transition can be compared to a standardized color chart to provide a quantitative measurement of the concentration of HLE, and therefore leukocyte cells, in the test sample.

Typically, the analyte detection device is a reagent-impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or a non-bibulous carrier matrix incorporating the reagent composition. In general, the carrier matrix is an absorbent material that allows the test sample to move, in response to capillary forces, through the carrier matrix to contact the reagent composition and produce a detectable or measurable color transition.

The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like cellulosic beads, and especially fiber-containing papers such as filter paper of chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. The handle usually is formed from a hydrophobic material such as cellulose acetate, polyethylene terephthalate, polycarbonate or polystyrene.

If the test strip is designed to assay HLE in a test sample, the carrier matrix can be any bibulous or nonbibulous material that allows the soluble components of the test sample to permeate and saturate the test pad of the test strip that is impregnated with the reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such carrier matrices possess all of the qualities required of a carrier matrix of the present invention, such as suspending and positioning the ingredients included in the reagent composition, and permeability of the soluble components of the test sample through the carrier matrix.

To achieve the full advantage of the present invention, the reagent composition is impregnated into a suitable carrier matrix and utilized in a dry phase test strip for the assay of leukocyte cells, esterase or protease in a test sample. The method of the present invention provides an economical, accurate and reliable assay, that can be performed at home or in the laboratory, for the presence or concentration of HLE, and therefore leukocyte cells, in a test sample. In addition, the method of the present invention allows detection, differentiation and measurement of a trace amount of leukocyte cells in the test sample, therefore making the assay more useful clinically.

In accordance with the method of the present invention, a test device was prepared which was sensitive to the presence of leukocyte esterase. An aqueous solution including 0.8M borate-sodium hydroxide buffer (pH 8.8) and 1% by weight of polyvinylpyrrolidone (PVP K-60 available from ISP Corp., Wayne, N.J.) first was prepared. A 4 inch wide strip of WHATMAN 3MM filter paper, available commercially from Whatman, Ltd., Maidenhead, Kent, U.K., then was impregnated with the aqueous solution. The impregnated filter paper strip next was dried in an Air Foil paper dryer, available from Thermoelectron, Kaukauna, Wis., at 79° C. to 121° C. for about 5 to 6 minutes.

The dried, impregnated filter paper strip then was impregnated a second time by immersion into an acetone solution containing 1.1 mM of a lactate ester of structural formula (IX)–(XIII), 0.7 mM 4-diazo-3-hydroxy-7-nitro-1-naphthylsulfonate (i.e., the compound of structural formula (XX), also named 6-nitro-1,2-naphthoquinone diazide), 1.5% (v/v) 1-decanol and 3% (v/v) dimethylsulfoxide. After the second impregnation, the filter paper strip was dried at 60° C. for about 5 to 6 minutes to provide an off-white filter paper strip. The dried, twice-impregnated filter paper pad is secured to an opaque or transparent hydrophobic plastic handle with double-sided adhesive tape. The dried and twice-impregnated filter paper strip was next cut to an appropriate size for a test strip assay, such as a pad having dimensions of about 0.2 in (inch) (0.5 cm) by about 0.2 in (0.5 cm).

It should be understood that it is well within the experimental techniques of those skilled in the art of preparing test devices to determine the proper balance between size of reagent pad, the strength of reagent composition solutions, the amount of test sample, and the method of introducing the test sample to the test strip, such as by pipetting rather than dipping, in order to design a quantitative assay for leukocyte cells, esterase or protease utilizing the method and composition the present invention.

In addition, it should be understood that the carrier matrix can be saturated or impregnated by immersing the carrier matrix into a single aqueous, or aqueous-organic solvent, solution including all of the essential and optional ingredients of the reagent composition. However, the two step method utilizing two immersions is preferred because particular reagent composition ingredients have relatively low water solubilities.

To perform an assay for leukocyte cells, esterase or protease, the resulting test strip is contacted with a urine sample for a sufficient time to saturate the test pad with the sample. After waiting a predetermined time, such as from about one to about two minutes, the test strip is examined, either visually or by instrument, for a response. A color transition in the test pad reveals the presence or concentration of leukocyte cells, esterase or protease in the test sample.

In many cases, simple visual observation of the test strip provides the desired information. If more accurate information is required, a color chart bearing color spots corresponding to various known concentrations of leukocyte cells can be prepared for the particular reagent composition used in the test strip. The resulting color of the test strip after contact with the test sample then can be compared with the color spots on the chart to determine the concentration of leuko-cyte cells in the test sample. In addition, the dry phase test strip assay can be made more accurate by employing instrumental spectrophotometric or colorimetric techniques, as opposed to visual techniques, to measure the degree and intensity of the color transition, especially at trace to low concentrations.

To demonstrate the new and unexpected results achieved by the method of the present invention, dry phase test strips incorporating a reagent composition of the present invention were used to assay standardized solutions including HLE. Individual test strips each incorporating one chromogenic lactate ester having a structural formula (X) through (XIV) and a diazonium salt coupling agent were quickly immersed into standardized solutions containing 0, 19 or 48 ng/mL HLE, then removed. Approximately two minutes after contacting a standardized HLE solution, the reflectance of the test pad of the test strip was measured at 557 nm (nanometers) on a CLINITEK® 10 clinical reflectance meter, available from Miles, Inc., Elkhart, Ind.

The reflectance, R, as taken from the reflectance scale of zero to one, was incorporated into the Kubelka-Munk function:

$$K/S = (1-R^2/2R),$$

wherein K is the absorption coefficient, S is the scattering coefficient and R is reflectance. The reflectance values determined at 557 nm were used to calculate the K/S values. The K/S values are proportional to test strip color, therefore the greater the K/S value, the greater the degree and intensity of the color transition of the test strip and the greater the concentration of HLE in the test strip.

Test strips, each incorporating a different chromogenic lactate ester having a structural formula (X) through (XIV), were compared to the corresponding amino acid ester, i.e., the alanine ester, for an ability to assay for HLE. For example, the L-form of the lactate ester of structural formula (X) has the structure

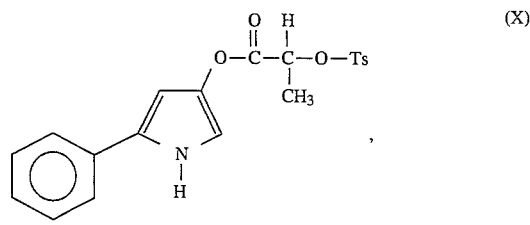

Lactate ester (X) was compared to the corresponding alanine compound (I) for an ability to assay urine for HLE, and therefore leukocyte cells, esterase or protease. The corresponding alanine compound (I) is used in the present day LEUKOSTIX® test strips.

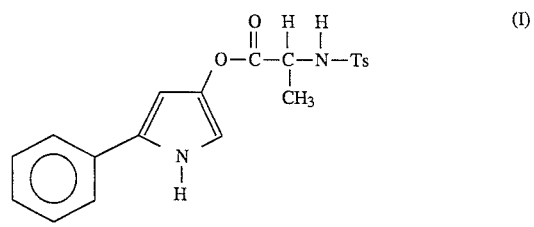

The lactate esters of structural formulae (XI)–(XIV) also were compared to a corresponding alanine ester.

Therefore, the following examples demonstrate the ability of chromogenic lactate esters of structural formula (VI), and particularly of structural formula (V), to act as a substrate for HLE, and thereby assay a test sample for leukocyte cells, esterase or protease. It is known that amino acid esters, like compound (I), have been used as colorimetric substrates to detect HLE. The following examples illustrate that the novel, non-amino acid, lactic acid-based colorimetric substrates of the present invention are readily hydrolyzed by a serine protease-based enzyme, like HLE, to provide a detectable and differentiable color transition.

EXAMPLE 6

Dry phase test strips incorporating the lactate ester of structural formula (X), and prepared as discussed above, were compared to dry phase test strips incorporating the corresponding alanine derivative (I) for an ability to detect HLE in urine. A comparison also was made between the diazonium salt coupling agents DNSA (XX) and NDNSA (XXI). The test strips were otherwise identical. The results tabulated below were obtained after quickly immersing the individual reagent strips into standardized HLE solutions. Two minutes after immersion, the test strips were examined for a chromogenic response as described above.

to HLE. In addition, the diazonium salt NDNSA (XXI) provides a larger K/S and a larger change in K/S than the diazonium salt DNSA (XX). Diazonium salts (XXII)–(XXVI) produced a K/S and change in K/S intermediate between diazonium salts (XX) and (XXI). Therefore, the combination of a lactate ester with the diazonium salt NDNSA (XXI) provides an enhanced ability to detect trace to low concentrations of leukocyte cells in a test sample compared to the presently-used alanine derivative (I).

EXAMPLE 7

Test strips incorporating the lactate ester of structural formula (XI) were compared to test strips incorporating the corresponding alanine derivative in an identical manner as described in Example 6. All test strips incorporated the diazonium salt NDNSA (XX). The assay results are summarized below.

|  |  | Response at 120 seconds | | | |
|---|---|---|---|---|---|
|  | HLE | R = Alanine | | R = Lactate (X) | |
| Compound | (ng/mL) | K/S | Change | K/S | Change |
| n-Pr—SO$_2$—R—OPP | 0 | 0.050 | — | 0.100 | — |
|  | 19 | 0.363 | 0.313 | 0.498 | 0.398 |
|  | 48 | 0.881 | 0.831 | 1.049 | 0.949 |

Similar to Example 6, the lactate ester of structural formula (X) provided a larger change in K/S than the corresponding alanine derivative, therefore providing a more sensitive assay for leukocyte cells, esterase or protease by providing

|  |  | Response at 120 seconds | | | |
|---|---|---|---|---|---|
|  | Diazonium | HLE: 0 ng/mL | | HLE: 19 ng/mL | |
| Substrate | Salt | K/S | Change | K/S | Change |
| Tosyl—Ala—OPP (I) | DNSA OM | 0.021 | — | 0.146 | 0.125 |
| Tosyl—Ala—OPP (I) | NDNSA (XXI) | 0.044 | — | 0.308 | 0.264 |
| Tosyl-(L)—Lac—OPP (X) | NDNSA (XXI) | 0.046 | — | 0.348 | 0.302 |

Surprisingly, the lactate ester of structural formula (X) is readily hydrolyzed by the enzyme HLE, thereby providing a color transition that is at least as intense as the alanine derivative of structural formula (I). The K/S value and the change in K/S value between 0 and 19 ng/mL HLE are greater for the lactate ester of structural formula (X) than the alanine derivative (I). The lactate ester of structural formula (X) therefore provides a more intense and differentiable color transition than the alanine derivative (I) in responding a more intense and more differentiable color transition.

EXAMPLE 8

Test strips incorporating the lactate ester of structural formula (XII) were compared to test strips incorporating the corresponding alanine derivative in an identical manner as described in Example 6. All test strips incorporated the diazonium salt NDNSA (XXI). The assay results are summarized below.

|  | | Response at 120 seconds | | |
| --- | --- | --- | --- | --- |
| | HLE | R = Alanine | | R = Lactate (XI) | |
| Compound | (ng/mL) | K/S | Change | K/S | Change |
| Ph—CO—R—OPP | 0 | 0.038 | — | 0.041 | — |
|  | 19 | 0.039 | 0.001 | 0.106 | 0.065 |

Similar to Examples 6 and 7, the lactate ester of structural formula (XII) provided a larger K/S and a larger change in K/S than the corresponding alanine derivative. The response for compounds including the benzoyl blocking agent, which has a carbonyl group, was not as great as compounds including a blocking agent having a sulfonyl group. This lower response is observed in the smaller change in K/S compared to the compounds tested in Examples 6, 7, 9 and 10. Therefore, alcohol blocking groups including a sulfonyl group and having the structure (VII) are preferred over alcohol blocking groups including a carbonyl group and having the structure (VIII).

EXAMPLE 9

Test strips incorporating the lactate ester of structural formula (XIII) were compared to test strips incorporating the corresponding alanine derivative in an identical manner as described in Example 6. All test strips incorporated the diazonium salt NDNSA (XXI). The assay results are summarized below.

|  | | Response at 120 seconds | | |
| --- | --- | --- | --- | --- |
| | HLE | R = Alanine | | R = Lactate (XII) | |
| Compound | (ng/mL) | K/S | Change | K/S | Change |
| CH₃O—CO(CH₂)₂—SO₂—R—OPP | 0 | 0.074 | — | 0.177 | — |
|  | 19 | 0.435 | 0.361 | 0.514 | 0.337 |
|  | 48 | 0.976 | 0.902 | 0.916 | 0.739 |

The K/S and change in K/S exhibited by the lactate ester of structural formula (XIII) were similar to the K/S and change in K/S of the corresponding alanine derivative at low esterase levels, but were less than the K/S and change in K/S exhibited by the corresponding alanine derivative at higher esterase levels. However, the K/S and change in K/S for the lactate ester of formula (XIII) are sufficient to assay for HLE.

EXAMPLE 10

Test strips incorporating the lactate ester of structural formula (XIV) were compared to test strips incorporating the corresponding alanine derivative in an identical manner as described in Example 6. The assay results are summarized below.

|  | | Response at 120 seconds | | |
| --- | --- | --- | --- | --- |
| | HLE | R = Alanine | | R = Lactate (XI) | |
| Compound | (ng/mL) | K/S | Change | K/S | Change |
| 2-Thiophene-SO₂—R—OPP | 0 | 0.050 | — | 0.03 | — |
|  | 19 | 0.224 | 0.174 | 0.385 | 0.332 |

Similar to Examples 6 through 8, the chromogenic lactate ester (XIV) exhibited a larger K/S and a larger change in K/S than the corresponding alanine derivative, therefore providing a more sensitive and accurate assay for leukocyte cells, esterase or protease in a test sample.

As demonstrated in Examples 6–10, chromogenic lactate esters of the present invention are capable of differentiating between the absence and presence of HLE in a test sample and are capable of measuring the concentration of HLE in a test sample. In addition, the chromogenic lactate esters perform comparably, and typically outperform, HLE substrates which contain the conventional amino acids, like the alanine derivative of structural formula (I). Therefore, the lactate esters of the present invention represent a new class of compounds useful in detecting leukocyte cells, or elastase or esterase activity, in biological fluids, such as urine.

Tests also were performed to determine the sensitivity of the chromogenic lactate esters to varying concentrations of HLE. The results are tabulated in Table 2, which compares assay results for the chromogenic lactate ester of structural formula (X) to its corresponding alanine derivative. All assays utilized the diazonium salt NDNSA (XXI).

TABLE 2

| HLE (ng/mL) | n-Pr—SO₂—Ala—OPP ΔK/S[1] (557 mm) at 120 seconds | n-Pr—SO₂—Lac—OPP |
|---|---|---|
| 5 | 0.065 | 0.108 |
| 10 | 0.165 | 0.257 |
| 20 | 0.353 | 0.533 |
| 100 | 1.474 | 1.462 |
| 200 | 1.797 | 1.693 |
| 500 | 1.628 | 1.915 |

[1]change in K/S between 0 ng/mL HLE and the indicated BLE concentration.

The alanine derivative can be used to assay for HLE over the range of 5 to 500 ng/mL (i.e., about 2 to about 175 cells/μL). Below 5 ng/mL, the color transition of the alanine derivative is not sufficiently intense to provide a differentiable response. In addition, there is no difference in response to solutions having 200 and 500 ng/mL HLE. Accordingly, a technician cannot readily differentiate between test sample containing 200, 500 or greater than 500 ng/mL of HLE.

However, as illustrated in Table 2, the present lactate esters exhibit a relatively high K/S in the presence of 5 ng/mL HLE, and therefore are capable of detecting lower levels of HLE in a test sample. In addition, the K/S value for the lactate ester (XI) continues to increase between 200 and 500 ng/mL HLE, thereby improving color transition differentiation, e.g., improving instrumental discrimination. In contrast, when using an alanine derivative, the color formation between 200 and 500 ng/mL HLE is sufficiently dark such that a technician would have difficulty differentiating between a test sample containing 200 or 500 ng/mL HLE. These results further demonstrate the increased sensitivity the present chromogenic lactate esters to low concentrations of HLE, thereby providing an accurate assay for leukocyte cells, esterase or protease over a broader concentration range.

The hydroxy-protected 5-phenyl-3-hydroxy-pyrrolyl-(L)-lactate esters of the present invention are a novel class of chromogenic esterase substrates having an increased, or comparable, reactivity to the corresponding 5-phenyl-3-hydroxy-pyrrolyl-tosyl-(L)-alaninate substrates, which are presently used in commercial test strip assays for leukocyte cells. The present lactate-based substrates for a serine protease-based enzyme are also new and advance the art. The present composition, method and device increase leukocyte cell assay sensitivity such that as little as 5 ng/mL of HLE can be detected within two minutes, thereby permitting improved detection of trace leukocyte cell levels. The present invention also has the advantage that readtime can be reduced from 120 to 60 seconds.

Obviously, many modifications and variations of the invention as hereinbefore set forth can be made without departing from the spirit and scope thereof and therefore only such limitations should be imposed as are indicated by the appended claims.

We claim:

1. A lactate ester having the structure

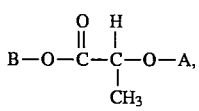

wherein A is an alcohol blocking group, and wherein B-O- is a residue of a compound B-OH and provides a detectable response when the lactate ester is hydrolyzed to generate the compound B-OH, wherein the detectable response is chromogenic, fluorescent, a reflectance change, a pH change, chemiluminescent, colorimetric, or spectrophotometric.

2. The ester of claim 1 wherein the compound B-OH is selected from the group consisting of a pyrrole, a thiophene, a furan, an azoresorcinol, a phenol, a leukoindophenol, an azo dye, 5-(4-hydroxy-3,5-dimethoxyphenylmethylene)-2-thioxothiazoline-3-acetic acid, a 2-substituted-6-hydroxybenzothiazole having the structure

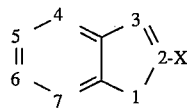

wherein:

a) at least one of the carbons of positions 4, 5, 6 or 7 is linked to a chemical moiety containing an anion group which is attached to the benzene ring; and;

b) the carbon at position 2 is linked to a chemical moiety comprised of at least two atoms which extend resonance of the benzothiazole ring system; and, c) a nitrogen atom is located at position 3; and d) a sulfur atom is located at position 1, a ω-nitrostyryl ester, a resorufin, an acridinone, a merocyanine, an 8-hydroxy-2H-dibenz-(b,f)azepin-2-one, a dibenzo azepinone, a dibenzothiazepinone, a coumarin ester, and mixtures thereof.

3. The ester of claim 1 wherein the compound B-OH comprises a pyrrole, a thiophene, a furan, or mixtures thereof.

4. The ester of claim 1 wherein A has a structure

wherein R³ is an alkyl group having 3 to about 22 carbon atoms or R³ is an aryl group.

5. The ester of claim 1 wherein A has a structure

wherein R³ is an alkyl group having 3 to about 22 carbon atoms or R³ is an aryl group.

6. The ester of any one of claims 4 and 5 wherein R³ is selected from the group consisting of phenyl, pyrrolyl, pyridyl, naphthyl, alkyl-substituted phenyl and alkoxy- substituted phenyl, wherein the alkyl or the alkoxy substituent has one to about 10 carbon atoms.

7. The ester of claim 1 wherein A is selected from the group consisting of p-toluenesulfonyl, n-propylsulfonyl, benzoyl, carbomethoxyethane sulfonyl, and thiophene sulfonyl.

8. The ester of claim 1 having the structure

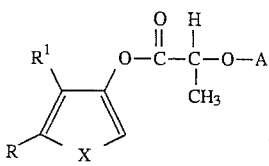

wherein A is an alcohol blocking group, X is O,S or $NR^2$, R is aryl or lower alkyl, $R^1$ is hydrogen or lower alkyl, and $R^2$ is hydrogen, lower alkyl or aryl.

9. The ester of claim 8 wherein A is selected from the group consisting of p-toluenesulfonyl, n-propylsulfonyl, benzoyl, carbomethoxyethane sulfonyl, and thiophene sulfonyl.

10. The ester of claim 8 wherein X is $NR^2$.

11. The ester of claim 10 wherein $R^2$ is hydrogen.

12. The ester of claim 8 wherein R is phenyl.

13. The ester of claim 8 wherein $R^1$ is hydrogen.

14. The ester of claim 1 having the structure

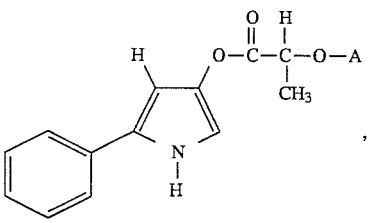

wherein A is selected from the group consisting of p-toluenesulfonyl, n-propylsulfonyl, benzoyl, carbomethoxyethane sulfonyl, and thiophene sulfonyl.

15. A composition for determining the presence or concentration of leukocyte cells, esterase or protease in a test sample, said composition comprising:

(a) a lactate ester having the structure

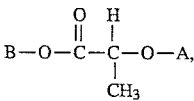

wherein A is an alcohol blocking group, and wherein B-O- is a residue of a compound B-OH, and provides a detectable response when the lactate ester is hydrolyzed to generate the compound B-OH, wherein the detectable response is chromogenic, fluorescent, a reflectance change, a pH change, chemiluminescent, colorimetric, or spectrophotometric;

(b) a buffer, (c) optionally, an accelerator compound capable of increasing the rate of hydrolysis of the lactate ester; and (d) optionally, a diazonium salt.

16. The composition of claim 15 comprising an accelerator compound capable of increasing the rate of hydrolysis of the lactate ester and a diazonium salt.

17. The composition of claim 16 wherein the diazonium salt is present in a concentration of about 0.1 to about 1 millimolar and the accelerator compound is present in an amount of about 0.1% to about 2% (v/v) of the composition.

18. The composition of claim 16 wherein the lactate ester has the structure

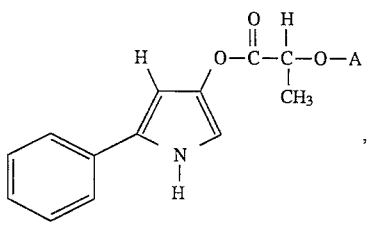

wherein A is selected from the group consisting of p-toluenesulfonyl, n-propylsulfonyl, benzoyl, carbomethoxyethane sulfonyl, and thiophene sulfonyl.

19. The composition of claim 15 wherein the compound B-OH is selected from the group consisting of a pyrrole, a thiophene, a furan, an azoresorcinol, a phenol, a leukoindophenol, an azo dye, 5-(4-hydroxy-3,5-dimethoxyphenylmethylene)-2-thioxothiazoline-3-acetic acid, a 2-substituted-6-hydroxy-benzothiazole having the structure

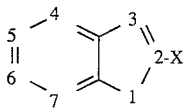

wherein:

a) at least one of the carbons of positions 4, 5, 6 or 7 is linked to a chemical moiety containing an anion group which is attached to the benzene ring; and;

b) the carbon at position 2 is linked to a chemical moiety comprised of at least two atoms which extend resonance of the benzothiazole ring system; and, c) a nitrogen atom is located at position 3; and d) a sulfur atom is located at position 1, a ω-nitrostyryl ester, a resorufin, an acridinone, a merocyanine, an 8-hydroxy-2H-dibenz-(b,f)azepin-2-one, a dibenzo azepinone, a dibenzothiazepinone, a coumarin ester, and mixtures thereof.

20. The composition of claim 15 wherein A has a structure

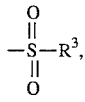

wherein $R^3$ is an alkyl group having 3 to about 22 carbon atoms or $R^3$ is an aryl group.

21. The compound of claim 15 wherein A has a structure

wherein $R^3$ is an alkyl group having 3 to about 22 carbon atoms or $R^3$ is an aryl group.

22. The composition of claim 15 wherein A is selected from the group consisting of p-toluenesulfonyl, n-propylsulfonyl, benzoyl, carbomethoxyethane sulfonyl, and thiophene sulfonyl.

23. The composition of claim 15 wherein the lactate ester has the structure

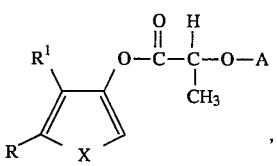

wherein X is O,S or $NR^2$, R is aryl or lower alkyl, $R^1$ is hydrogen or lower alkyl, and $R^2$ is hydrogen, lower alkyl or aryl.

24. The composition of claim 23 wherein X is $NR^2$.

25. The composition of claim 24 wherein $R^1$ and $R^2$ are hydrogen and R is phenyl.

26. The composition of claim 25 where A is p-toluenesulfonyl or n-propylsulfonyl.

27. The composition of claim 15 wherein the lactate ester is present in a concentration of about 0.5 to about 2 millimolar.

28. The composition of claim 15 wherein the buffer provides a pH of about 7 or greater, said pH being in a range wherein the lactate ester is capable of being hydrolyzed.

29. The composition of claim 15 wherein the buffer provides a pH of about 7 to about 10.

30. The composition of claim 15 wherein the buffer is present in a concentration of about 200 to about 600 millimolar.

31. The composition of claim 15 wherein the accelerator compound is present in an amount of 0 to about 4% (v/v) of the composition.

32. The composition of claim 15 wherein the accelerator compound comprises an aliphatic alcohol having 3 to about 15 carbon atoms.

33. The composition of claim 15 wherein the diazonium salt is present in a concentration of 0 to about 2 millimolar.

34. The composition of claim 15 wherein the diazonium salt has the structure

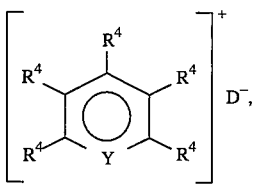

wherein $R^4$, either the same or different, is hydrogen, lower alkyl or aryl, or wherein two adjacent $R^4$ groups together form a fused ring system, with the proviso that one of $R^4$ is $-N^+{\equiv}N$; Y is N or $CR^5$, wherein $R^5$ is hydrogen or lower alkyl; and $D^-$ is an anion.

35. The composition of claim 15 wherein the diazonium salt has the structure

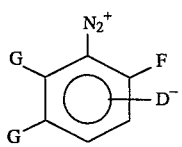

wherein F is hydrogen, lower alkyl or hydroxy; $D^-$ is a covalently bound anion; G, either the same or different, is hydrogen, lower alkyl or aryl, or both G groups taken together from a fused ring system.

36. The composition of claim 35 wherein the accelerator compound comprises an aliphatic alcohol having about 8 to about 15 carbon atoms, and the diazonium salt is selected from the group consisting of 1-diazo-2-naphthol-4-sulfonate, 4-diazo-3-hydroxy-7-nitro-1-naphthyl sulfonate, and mixtures thereof.

37. The composition of claim 15 wherein the diazonium salt is selected from the group consisting of 1-diazo-2-naphthol-4-sulfonate, 1-diazophenyl-3-carbonate, 4-diazo-3-hydroxy-1-naphthylsulfonate, 4-diazo-3-hydroxy-7-nitro-1-naphthylsulfonate, 4-diazo-3-hydroxy-1,7-naphthyldisulfonate, 2-methoxy-4-(N-morpholinyl)benzene diazonium chloride, 4-diazo-3-hydroxy-7-bromo-1-naphthylsulfonate, 4-diazo-3-hydroxy-7-cyano-1-naphtylsulfonate, 4-diazo-3-hydroxy-7-1-naphthylsulfonate, and mixtures thereof.

38. The composition of claim 15 further comprising 0% to about 4% by weight of a polymeric material selected from the group consisting of polyvinylpyrrolidone, polyvinyl alcohol, gum arabic, gelatin, algin, carrageenan, albumin, a cellulose and mixtures thereof, 0% to about 0.4% by weight of a surfactant, or mixtures thereof.

39. A composition which exhibits a sufficient color transition upon contacting a test sample to demonstrate a presence or concentration of leukocyte cells in the test sample, said composition comprising:

(a) about 0.5 to about 1.5 mM of a chromogenic lactate ester having the structure

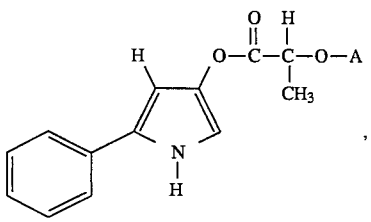

wherein A is selected from the group consisting of p-toluenesulfonyl, n-propylsulfonyl, benzoyl, carbomethoxyethane sulfonyl, and thiophene sulfonyl;

(b) a buffer capable of providing a pH of about 7 to about 10;

(c) about 0.1% to about 2% (v/v) of an aliphatic alcohol having about 8 to about 15 carbon atoms; and (d) about 0.1 to about 1 mM of a diazonium salt coupling agent selected from the group consisting of 1-diazo-2-naphthol-4-sulfonate, 1-diazophenyl-3-carbonate, 4-diazo-3-hydroxy-1-naphthylsulfonate, 4-diazo-3-hydroxy-7-nitro-1-naphthylsulfonate, 4-diazo-3-hydroxy-1,7-naphthyldisulfonate, 2-methoxy-4-(N-morpholinyl)benzene diazonium chloride, 4-diazo-3-hydroxy-7-bromo-1-naphthylsulfonate, 4-diazo-3-hydroxy-7-cyano-1-naphthylsulfonate, and 4-diazo-3-hydroxy-7-1-naphthylsulfonate, and mixtures thereof.

40. A method of assaying a liquid test sample for the presence or concentration of leukocyte cells, esterase or protease comprising:

(a) contacting the liquid test sample with a reagent composition, said reagent composition comprising:

(i) a lactate ester having the structure

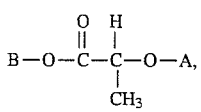

wherein A is an alcohol blocking group, and wherein B-O- is a residue of a compound B-OH and provides a detectable response when the lactate ester is hydrolyzed to generate the compound B-OH, wherein the detectable response is chromogenic, fluorescent, a reflectance change, a pH change, chemiluminescent, colorimetric, or spectrophotometric;

(ii) a buffer,
(iii) optionally, an accelerator compound, which increases the rate of hydrolysis of lactate ester, and
(iv) optionally, diazonium salt coupling agent;

(b) examining the reagent composition for a detectable response; and (c) correlating the detectable response to the presence or concentration of leukocyte cells, esterase or protease in the liquid test sample.

41. The method of claim 40 wherein the test sample is assayed for intact and lysed leukocyte cells.

42. The method of claim 40 wherein the presence or concentration of esterase or protease is correlated to the presence or concentration of lysed and intact leukocyte cells.

43. The method of claim 40 wherein the esterase is human leukocyte elastase.

44. The method of claim 40 wherein the liquid test sample is urine.

45. The method of claim 40 wherein the detectable response is a chromogenic response.

46. The method of claim 49 wherein the reagent composition is examined visually or instrumentally for a detectable response.

47. The method of claim 40 wherein the reagent composition detects and measures an esterase or protease concentration of about 5 to about 500 nanograms per milliliter of the test sample.

48. The method of claim 47 wherein the esterase or protease concentration is correlated to a leukocyte cell concentration of about 2 to about 175 cells per microliter of the test sample.

49. The method of claim 40 wherein the reagent composition is examined for a response about one minute after contacting the test sample.

50. The method of claim 40 wherein the reagent composition comprises an accelerator compound which increases the rate of hydrolysis of the lactate ester and a diazonium salt coupling agent.

51. The method of claim 50 wherein the lactate ester has the structure

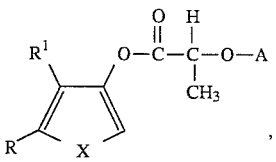

wherein X is O,S or $NR^2$, R is aryl or lower alkyl, $R^1$ is hydrogen or lower alkyl, and $R^2$ is hydrogen, lower alkyl or aryl.

52. The method of claim 51 wherein the lactate ester has the structure

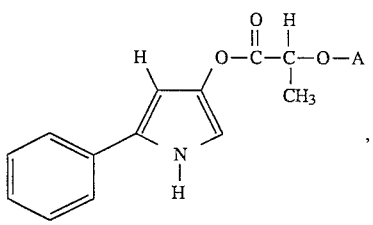

wherein A is selected from the group consisting of p-toluenesulfonyl, n-propylsulfonyl, benzoyl, carbomethoxyethane sulfonyl, and thiophene sulfonyl.

53. The method of claim 52 wherein the accelerator compound comprises an aliphatic alcohol having about 8 to about 15 carbon atoms, and the diazonium salt coupling agent is selected from the group consisting of 1-diazo-2-naphthol-4-sulfonate, 4-diazo-3-hydroxy-7-nitro-1-naphthyl sulfonate, and mixtures thereof.

54. The method of claim 40 wherein the assay for the presence or concentration of leukocyte cells, esterase or protease is a dry phase assay.

* * * * *